United States Patent [19]

Meili

[11] 4,166,960

[45] Sep. 4, 1979

[54] SMOKE DETECTOR

[75] Inventor: Ernst Meili, Küsnacht, Switzerland

[73] Assignee: Cerberus AG, Männedorf, Switzerland

[21] Appl. No.: 858,397

[22] Filed: Dec. 7, 1977

[30] Foreign Application Priority Data

Dec. 23, 1976 [CH] Switzerland .................... 16178/76

[51] Int. Cl.$^2$ .......................................... G01N 21/26
[52] U.S. Cl. .................................. 250/574; 250/575; 340/630
[58] Field of Search ............... 340/630; 356/207, 208; 250/574, 575, 237 R

[56] References Cited

U.S. PATENT DOCUMENTS

| | | | |
|---|---|---|---|
| 3,922,655 | 11/1975 | Lecuyer .............................. | 340/630 |
| 3,936,814 | 2/1976 | Muller-Girard et al. ............ | 250/574 |
| 4,021,792 | 5/1977 | Ludt et al. ........................... | 356/207 |

Primary Examiner—David C. Nelms
Attorney, Agent, or Firm—Werner W. Kleeman

[57] ABSTRACT

A smoke detector comprising a radiation source producing a directed radiation beam and a scattered radiation receiver arrangement having directional characteristics. An evaluation circuit is operatively connected with the receiver arrangement for delivering a signal whenever there is exceeded a predetermined degree of radiation scattered at smoke particles within the radiation beam. Either the radiation source, the radiation receiver arrangement, or both, have such directional characteristic and the evaluation circuit is constructed such that the radiation received from two fields of view of the radiation receiver arrangement are compared with one another. These two fields of view are differently situated relative to the radiation beam and both fields of view contain a markedly different amount of scattered radiation, but receive at least approximately the same spurious radiation from at least approximately the same background.

30 Claims, 8 Drawing Figures

SMOKE DETECTOR

BACKGROUND OF THE INVENTION

The present invention relates to a new and improved construction of an optical smoke detector which is of the type comprising a radiation source which produces a directed bundle or beam of radiation, a scattered radiation-receiver arrangement having directional characteristic, and an evaluation circuit connected with the radiation receiver arrangement for delivering signals when the radiation scattering at the smoke particles in the radiation beam exceeds a predetermined value or degree.

With such type smoke detectors it is possible to detect or measure electromagnetic radiation which is scattered at small particles suspended in a medium. As the radiation there can be beneficially employed, for instance, light, infrared or ultraviolet radiation. As the medium there can be used different types of transparent gases, for instance air, or also liquids.

A particularly useful field of application of such detectors is as fire alarms, wherein the smoke particles suspended in air can be detected and by means of an evaluation circuit there can be triggered an alarm signal whenever the intensity of the smoke, and thus the intensity of the scattered radiation, exceeds a predetermined value. With such scattered radiation or smoke detectors, extreme care must be taken to ensure that the radiation receiver is not disturbed by other radiation. In order to prevent, for instance, radiation emanating from the surroundings from impinging upon the receiver, such equipment is therefore equipped with a light impervious housing surrounding the bundle or beam of radiation. Internally of the housing measures must be provided for extensively absorbing the radiation at those locations where the radiation beam impinges upon the inner wall of the housing, for instance with the aid of suitable radiation traps. Notwithstanding these measures, it is impossible to prevent that, for instance, due to reflection or bending of the incident radiation, the radiation receiver nonetheless receives a certain amount of spurious or unwanted radiation. With such detectors of the state-of-the-art it therefore was not possible to record scattered radiation of low intensity, and the sensitivity could not be increased to an extent as would be necessary for many fields of application.

Now in order to eliminate such drawback it has already been proposed to provide prior art smoke detectors with two radiation receivers, the fields of view of which detect different parts of the radiation beam, which are located at different distances from the radiation source, and in the presence of smoke, at which the scattered radiation intensity differs. By providing logical circuitry an alarm signal only then is triggered when the received intensities of the scattered radiation are in a proper correlation or relationship to one another. Since the fields of view of both receivers however encompass different wall regions of the detector housing it is not possible to eliminate different reflection characteristics at these locations which, for instance, can be caused by dissimilar dust deposits.

According to another prior art smoke detector there is likewise provided two radiation receivers arranged within a measuring housing and at which impinge different proportions of scattered radiation caused by penetration of smoke into the measuring housing. One of the radiation receivers faces the radiation beam, whereas the other radiation receiver faces away from the radiation beam so that it only receives the scattered radiation which is reflected at the housing wall. Also in this case both of the scattered radiation receivers are directed towards different parts of the housing, i.e., the one scattered radiation receiver detects reflections occurring at the rear of the other receiver. This construction equally does not ensure that both radiation receivers will truly receive the same amount of spurious radiation in the presence of scattering particles or smoke. Also with such detector it is possible for the presence of smoke to be falsified due to different reflection characteristics of the walls or housing parts which are located in the fields of view of both scattered radiation receivers.

SUMMARY OF THE INVENTION

Hence, with the foregoing in mind it is a primary object of the present invention to provide a new and improved construction of smoke detector which is not associated with the aforementioned drawbacks and limitations of the prior art constructions.

Another and more specific object of the present invention aims at eliminating or extensively suppressing the aforementioned drawbacks of the prior art scattered radiation or smoke detectors, and in particular relates to the provision of a detector which is insensitive to spurious radiation and is less influenced or not at all by deposition of dust or other contaminants at random locations.

Still a further significant object of the present invention aims at the provision of a new and improved smoke detector which is relatively simple in construction and design, economical to manufacture, extremely reliable in operation, and provides a high degree of integrity in detecting smoke particles in an atmosphere which are indicative of a combustion process.

Now in order to implement these and still further objects of the invention, which will become more readily apparent as the description proceeds, the smoke detector of the present development is manifested by the features that the radiation source and/or the scattered radiation receiver arrangement has such directional characteristic, and the evaluation circuit is constructed such, that the radiation received from two fields of view of the scattered radiation-receiver arrangement, which fields of view are differently located relative to the radiation beam, are compared with one another, and both fields of view have a markedly different proportion of scattered radiation, but receive at least approximately the same spurious radiation from at least approximately the same background.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE PREFERRED EMBODIMENTS

Figure 1A:
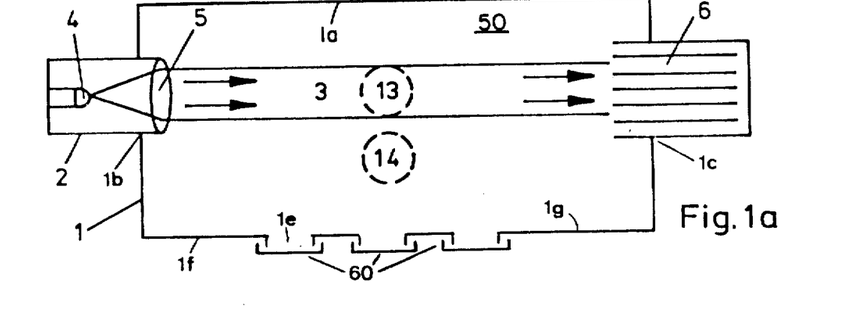
FIG. 1a is a vertical sectional view of a first exemplary embodiment of smoke detector shown in FIG. 1c, the section being taken in a vertical plane of the detector housing through the region of the radiation source and its essentially oppositely situated radiation trap.
Figure 1B:
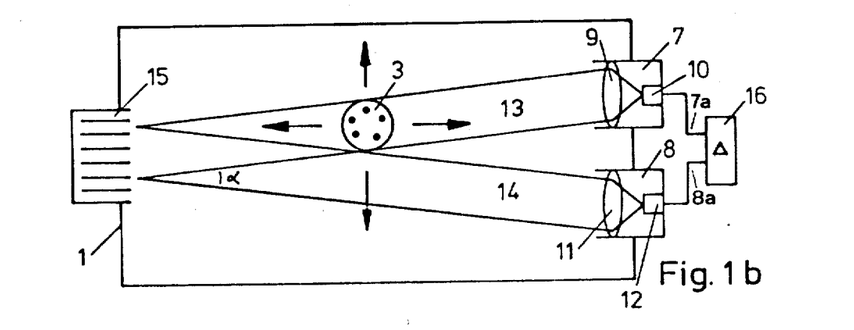
FIG. 1b is a vertical sectional view, like the showing of FIG. 1a, of the smoke detector shown in FIG. 1c, but through a different vertical plane containing the radiation receiver arrangement and oppositely located radiation impingement location.
Figure 1C:
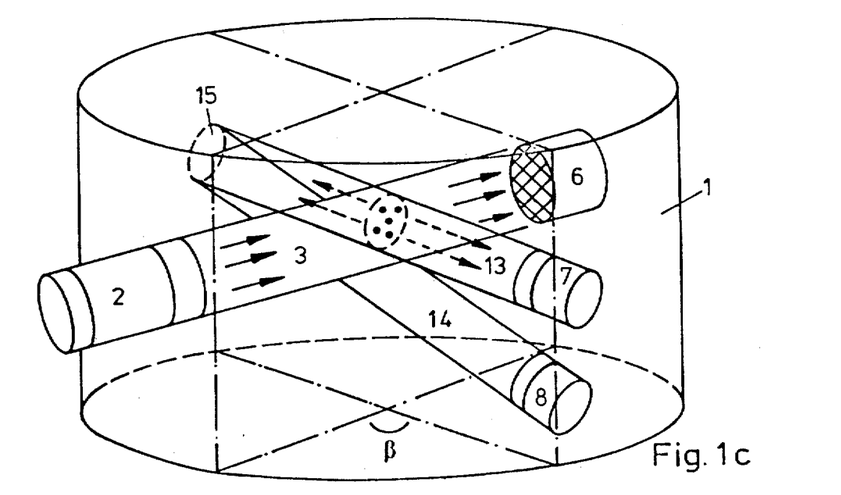
FIG. 1c is a schematic perspective view of the smoke detector shown in FIGS. 1a and 1c.

Describing now the drawings, the exemplary embodiment of smoke detector illustrated in FIGS. 1a-1c will be seen to comprise for instance a substantially cylindrical housing 1 which may be conventionally designed to have a housing wall 1f provided with apertures 1e covered by baffles 60 or equivalent structure which renders the housing 1 impervious to light, yet allows the entry of an external atmosphere to the supervised, such as air, which contains smoke into the detection chamber or compartment 50 thereof. The inner walls 1a of the housing 1 are constructed to absorb radiation, for instance blackened and/or at least partially provided with radiation-absorbing ribs. Thus, reference character 1g designates, for instance, a blackened wall or radiation absorbing coating. While conventional procedures may be employed for constructing the housing 1 to enable it to be impervious to external light but still permit the penetration of an atmosphere containing smoke particles therein, one possible construction and arrangement of such housing has been shown for instance in the commonly assigned U.S. Pat. No. 3,316,410, granted Apr. 25, 1967, to which reference may be readily had and the disclosure of which is incorporated herein by reference.

Now at one location of the cylinder or housing wall 1f, such as the location 1b, there is mounted a suitable radiation source 2 which transmits a radiation beam or bundle 3 transversely through the housing or detection chamber 50. The radiation source 2 can be, for instance, a laser which inherently transmits a sharp focused beam of radiation, or there can be utilized an otherwise conventional radiation source, for instance, an incandescent lamp or light-emitting diode, generally indicated by reference character 4. The radiation emitted by the radiation source 2, regardless of the nature thereof, is focused by a lens or optical system 5 into a radiation beam 3 with as sharply defined boundaries as possible. At the location 1c of the wall 1a of the housing 1, which is opposite the location 1b where there is mounted the radiation source 2, there is arranged a radiation trap 6 which absorbs as good as possible the incident radiation.

Now at another location of the cylinder wall 1a externally of the radiation beam 3, there is mounted a radiation receiver arrangement 7, 8 having a first radiation receiver 7. This radiation receiver 7, like the radiation source 2, possesses a directional characteristic which, for instance, can be produced by a lens or optical means 9 which focuses the incident radiation upon a photoelement 10. The field of view 13 of this radiation receiver 7 is aligned such that it intersects at the center of the radiation beam 3 and, thus, at least partially detects part of the radiation beam 3. At the location 15, opposite the radiation receiver 7, the wall 1a of the housing 1 is constructed to be radiation-absorbing, for instance blackened in conventional manner as previously explained, so that the scattered or spurious radiation which impinges at this location 15 is only detected in an extremely small amount by the field of view 13 of the radiation receiver 7. In the normal case, as long as no smoke is located in the radiation beam 3, the radiation receiver 7 therefore only detects a very small radiation intensity. If, however, smoke penetrates into the housing 1, then the radiation within the radiation beam 3 will be scattered at the smoke particles and the scattered radiation in the field of view 13 will be received by the radiation receiver 7. The evaluated scattering angle, corresponding to the intersection angle $\beta$ between the radiation beam 3 and the viewing field 13, can be appropriately selected in accordance with the scattering characteristics of the particles to be detected. In the case of smoke detectors it is advantageous to select this angle $\beta$ to be greater than 90°, preferably to amount to about 135°.

Neighboring the radiation receiver 7, the radiation receiver arrangement possesses a further radiation receiver 8 which likewise has a directional characteristic, for instance in that the incident radiation is focused by an optical element or system 11 upon a photoelement 12. The field of view 14 of this further radiation receiver 8 is aligned or directed such that it does not contact the radiation beam 3, rather just moves past its edge. A particularly advantageous arrangement can be realized if the radiation receiver 8 is located and aligned such that the field of view 14 emanates from the same wall location 15 as the field of view 13. In this way there is achieved the beneficial result that in the field of view 14 there is only received the residual radiation from this wall section 15, whereas in the field of view 13 there is received, apart from the residual radiation transmitted by the wall section 15, also the scattered radiation from the radiation beam 3.

The outputs 7a and 8a of both radiation receivers 7 and 8, respectively, are connected to an evaluation circuit 16 which contains a difference forming element or differential amplifier, and, if necessary, there can be arranged forwardly in circuit therewith, preamplifiers for the output signals of both radiation receivers 7 and 8 for the purpose of mutually tuning the sensitivity. Details of a possible construction of signal evaluation circuit 16 which can be used to advantage with not only the smoke detector of FIGS. 1a to 1c, but also the smoke detector to be considered with reference to FIG. 2, have been shown and will be discussed fully later on in this disclosure with reference to FIG. 5. Due to such difference forming operation the residual spurious radiation emanating from the wall section 15 is completely eliminated, so that there only remains the actual scattered radiation for further evaluation. What is of advantage in this regard is that both radiation receivers 7 and 8 are directed towards the same wall section 15 and the angle $\alpha$ between both receiving directions or fields of view 13 and 14 is extremely small, so that it can be expected that the spurious radiation in the directions or fields 13 and 14 is practically the same, rendering possible complete cancellation.

The drawback of the heretofore known smoke detectors, where the radiation receivers receive spurious radiation due to different reflection properties and which can exhibit different degrees of dust contamination, is thus here incipiently avoided.

With the previously described exemplary embodiment, the radiation source 2 and both of the radiation receivers 7 and 8 were constructed such that equally the radiation beam 3 and the fields of view or receiving directions 13 and 14 are extensively in the form of parallel beams or bundles. Although, for instance, the use of a radiation beam having sharply defined limits or outer contour, as such is produced by a laser, can be of advantage, the principles of the invention are not in any way limited to the use of parallel beams for the radiation beam and the viewing fields.

Figure 2:
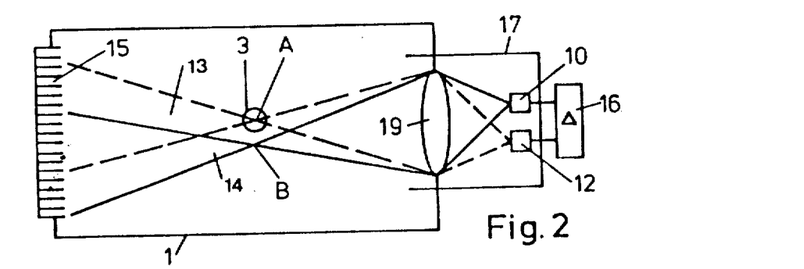
FIG. 2 is a vertical sectional view of a second exemplary embodiment or smoke detector having a simplified radiation receiver arrangement.

As shown in the modified smoke detector construction of FIG. 2, the fields of view 13 and 14 also can be constructed such that they have a certain aperture angle or are focused upon a spot or point. The same moreover is true for the radiation beam 3. In the illustrated embodiment there is provided a simplified radiation receiver arrangement 17 having a single lens 19 and two radiation receiving elements 10 and 12. The focal length of the lens 19 and the spacing of the radiation receiver elements 10 and 12 is selected such that both of the fields of view 13 and 14 have a focus or a minimum cross-sectional area at the points A and B, and the focus or focal point A is located within the radiation beam 3 and the focus or focal point B directly neighboring and outside of such radiation beam. This radiation beam 3 is likewise concentrated at the scanning point A. Because in this way there is obtained a particularly sharp transition of the radiation intensity from the radiation beam to the surroundings and the boundaries of the viewing fields are equally especially sharply defined, it is possible to obtain an optimum effect by employing these measures.

Figure 3:
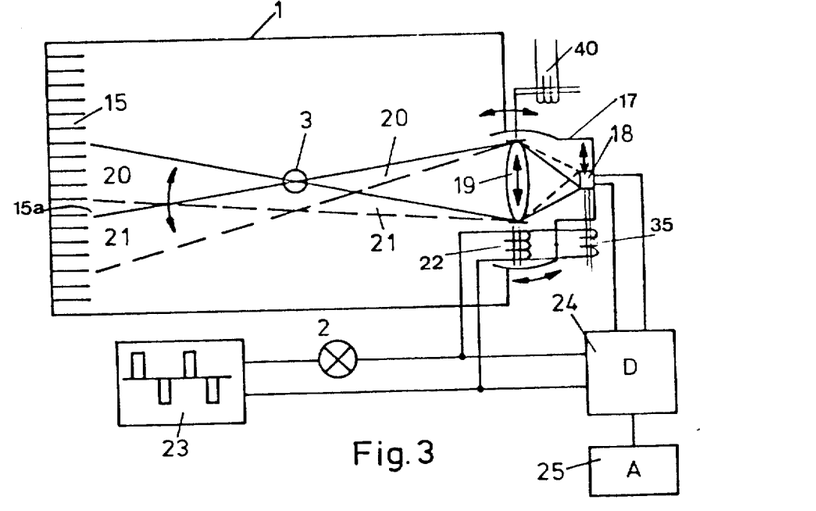
FIG. 3 is a vertical sectional view of a third exemplary embodiment of smoke detector having only one radiation receiver with pivotable or shiftable field of view.

While with the previously described exemplary embodiments two radiation receiving elements had to be provided in the radiation receiver arrangement, the embodiment illustrated in FIG. 3 portrays a smoke detector having one radiation receiver arrangement 17 which contains only a single photoelectric element 18 cooperating with an optical system or lens 19. In order with this embodiment to be able to also compare the radiation received from two fields of view which differ relative to the radiation beam 3, the field of view can be rocked into two extreme positions 20 and 21. As will be seen by referring to the left-hand side of FIG. 3, portions of the wall section 15 scanned by both such fields of view overlap i.e., part of the wall section 15 is within each field of view when shifted between the two extreme positions 20 and 21, as generally indicated by reference character 15a. This can be accomplished either by having the photoelectric element 18 displaceable in vertical direction or else the lens 19 in vertical direction, by using any suitable displacement elements, such as the respective electromagnets 35 and 22. However, instead of this solution there also can be provided a construction wherein the entire radiation receiver arrangement 17 can be tilted about a horizontal axis, such as by using the electromagnet 40. In this connection it can be advantageous to operate in a pulse-like manner the radiation source so that it is only turned-on when the shiftable field of view is located in one of both extreme positions. For this purpose, as shown, the radiation source 2 and the electromagnets 22, 35 and 40 can be operated by the same pulse transmitter 23. The apparatus becomes particularly simple if the pulse transmitter 23 periodically alternately delivers positive and negative pulses, and the electromagent intended to be energized moves the displaceable part back-and-forth in the same cycle or rhythm. The evaluation circuit 24 which is connected with the photoelectric element 18 is synchronized by the pulse transmitter 23 and evaluates the received radiation intensities separately during the pulses of positive and negative polarity, for example by means of two anti-parallel evaluation channels, having a time-constant which is greater than the pulse interval or pause, and again, there is formed the difference of the signals in both of these evaluation channels. A particularly energy-saving arrangement is realized for the periodic rocking or pivoting of the field of view if the movable part of the radiation receiver arrangement 17, for instance, the photoelectric element 18 or the lens element 19 are resiliently mounted in such a manner that the resonance frequency of the system coincides with the pulse frequency or the system works according to the oscillating armature or swing lever principle.

Figure 4:
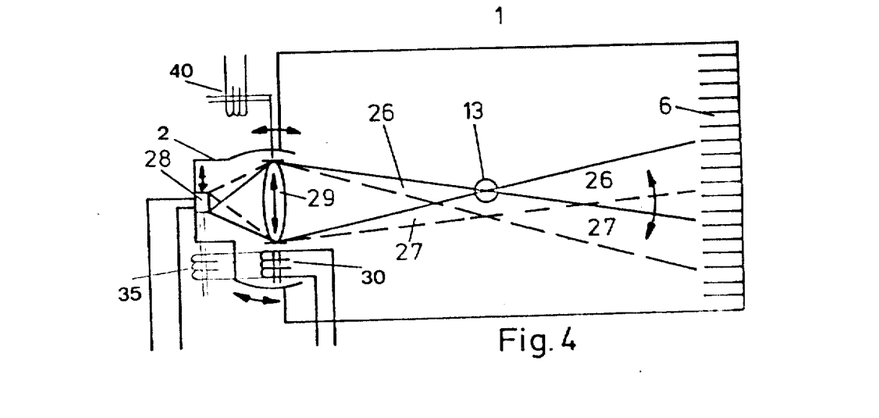
FIG. 4 illustrates a fourth exemplary embodiment of smoke detector having only one radiation receiver with a fixed field of view and a pivotable radiation beam.

As illustrated in FIG. 4 it is however possible, instead of pivotably constructing the field of view to also pivotably construct the radiation emitting part of the system such that the radiation beam can be rocked from one extreme position 26 into the other extreme position 27. To this end, the radiation source 2 can be constructed exactly analogous to the radiation receiver arrangement 17 of FIG. 3. For instance, either the radiation emitting element 28 or the lens element 29 can be displaced in vertical direction by the electromagnets 35 and 22 respectively, or the entire radiation source 2 is tiltable about a horizontal axis, as by means of the electromagnet 40. As mentioned, these movements can be accomplished by means other than the exemplary considered electromagnets, it only being of importance that the radiation beam can rock between two extreme positions 26 and 27. In this case, there is provided only a single radiation receiving-field of view 13 with only a single radiation receiver.

In both instances the fluctuation of the field of view or the radiation beam, as the case may be, can occur periodically from one extreme position to the other and back again, and the portion of the alternating-current voltage of the output signal of the radiation receiver, i.e., the difference between the maximum and minimum, constitutes a measure for the scattered radiation intensity and the smoke density. However, it is possible for the evaluation to be accomplished also in such a manner that the pivoting of the field of view or the radiation beam from one extreme position into the other occurs at certain times, and the change of the outpt signal, in other words the difference from the starting value, constitutes a measure for the smoke density. The evaluation operation becomes especially non-susceptible to disturbances if the evaluation circuit 24 is synchronized with the pulse transmitter 23. Details of a possible construction of evaluation circuit usable with the embodiments of smoke detectors of FIGS. 3 and 4, will be considered fully shortly with reference to FIG. 6.

Both arrangements have the advantage that only one single radiation receiver is required. Since also with this embodiment, like with the embodiment of FIG. 3, the radiation receiver receives a markedly different amount of scattered radiation from the radiation beam in both extreme positions and at the same time the spurious radiation is taken-up by at least approximately the same or partially similar backgrounds, a smoke detector constructed according to this embodiment is also capable of extensively operating without being affected by spurious radiation or dust deposits internally thereof.

With all of the exemplary embodiments there can be used as the evaluation circuit a random construction of appropriate difference-forming circuitry. For instance, when using the equipment as a measuring device for determining the concentration of aerosols or suspended particles in a medium, it is advantageous to select an analogue output for the difference-forming circuits or evaluation circuits 16 and 24, by means of which there can be directly indicated the concentration. When using the system as an alarm device, for instance as a smoke detector in the fire alarm field, it is advantageous to provide a threshold value detector which delivers a signal to an alarm device 25 as soon as the output signal of the difference forming circuits 16 or 24 exceeds a predetermined threshold value.

Figure 5:
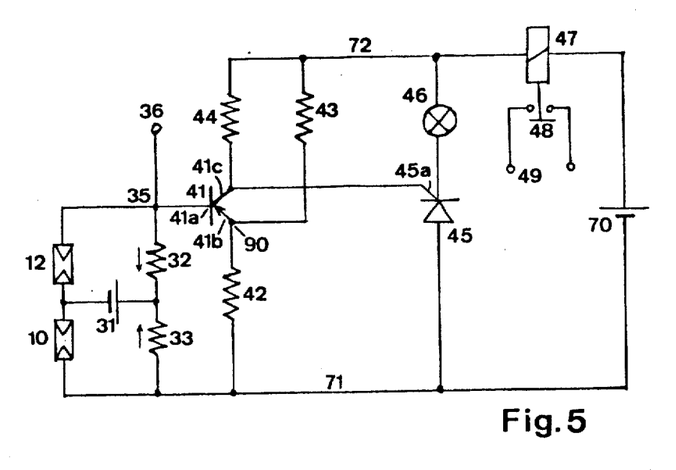
FIG. 5 illustrates details of an evaluation circuit which can be employed with the smoke detectors of FIGS. 1a-1c and FIG. 2.

Turning now to FIG. 5 there is illustrated an evaluation circuit arrangement as the same can be advantageously employed with the embodiments of smoke detectors illustrated in FIGS. 1a-1c and FIG. 2. The photoelectric elements 10 and 12, which, for instance, may be photoresistors, are each connected by means of a respective resistor 32 and 33 and a common voltage source 31 into a respective closed current circuit, as shown. Both of these current circuits are oppositely poled. Since currents flow in opposite directions through the resistors 32 and 33 there appears at the output junction or terminal 35 the difference of the voltage or potential drop across the resistors 32 and 33 and the difference of the output voltages of the photoelectric elements 10 and 12. This difference voltage can be tapped-off at an output terminal 36 connected with the output 35 of the difference-forming or difference circuit.

Furthermore, the output point or junction 35 of the difference circuit is connected with the base 41a of a transistor 41, the emitter 41b of which is connected at the center tap 90 of a voltage divider composed of the resistors 42 and 43 and connected across the lines or conductors 71 and 72, whereas the collector 41c is connected by a resistor 44 with the line 72. The lines 71 and 72 are powered by a direct-current voltage from a suitable voltage source 70.

The collector 41c of the transistor 41 is connected with the control electrode 45a of a thyristor 45 which, in turn, is connected in series with an indicator or display lamp 46 likewise between the lines or conductors 71 and 72. Now as soon as the difference of the output signals of both photoelectric elements 10 and 12 has reached a predetermined value and there appears at the output terminal or junction 35 a difference voltage which exceeds the threshold voltage of the transistor 41, then current flows through transistor 41 and a voltage drop appears across the resistor 44. As soon as this voltage exceeds the ignition voltage of the thyristor 45, such becomes conductive and draws current which illuminates the lamp 46, energizes the relay 47 arranged at the line or conductor 72 and actuates its contact 48, thereby activating a suitable alarm device 49 which is connected with the relay terminals.

It is here mentioned that instead of employing the illustrated circuit, disclosed by way of example, it would be equally possible to use any other known difference forming circuitry.

Figure 6:
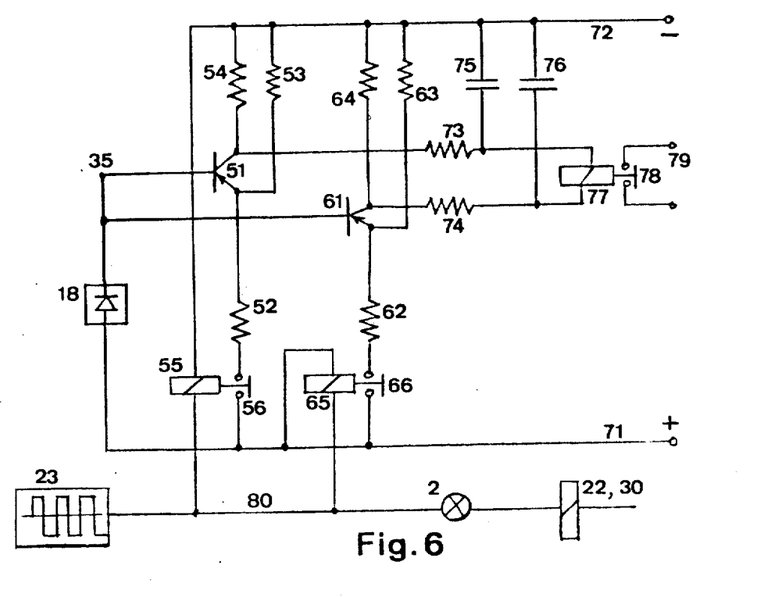
FIG. 6 illustrates an evaluation circuit which can be used with the exemplary embodiments of smoke detectors shown in FIGS. 3 and 4.

Now with the circuit shown in FIG. 6, which is particularly suitable for the exemplary embodiments of smoke detectors of FIGS. 3 ad 4, the here required sole photoelectric element 18 is constructed as an active component, i.e., it delivers an output voltage corresponding to the received radiation intensity. For instance, the photoelectric element 18 can be a solar cell.

The output terminal 35 of the difference circuit, in the embodiment disclosed, is connected with two different evaluation channels, each of which contains a separate transistor stage analogous to the single transistor stage of FIG. 5. Each of the transistor stages will be seen to comprise a respective transistor 51 and 61, a respective voltage divider 52, 53 and 62, 63 and a respective collector resistor 54 and 64. Additionally, however, there is here provided in the connection lines or conductors of both transistor stages leading to the line 71 a respective switching device 56 and 66 actuated by a respective relay device 55 and 65. The first relay device 55 is controlled by the pulse transmitter 23 in such a manner that it closes the contact 56 during the duration of the positive pulses and thus connects the transistor 51 across the lines 71 and 72. The other relay device 65 is actuated such that its contact 66 is only closed during the duration of the pulses of negative polarity and, thus, only connects the other transistor 61 across the lines 71 and 72 during this period of time.

The outputs of transistors 51 and 61 are each connected to a respective integration element composed of a charging resistor 73 and 74 and an integration capacitor 75 and 76, respectively. The time-constants of both RC-elements 73, 75 and 74, 76 respectively, are selected such that they are considerably greater than the pulse pauses or intervals of the pulse transmitter 23.

Both of the capacitors 75 and 76 thus receive during the relevant current conducting phases of both transistors 51 and 61 a respective charging pulse corresponding to the charging time of both transistors, i.e., in accordance with the irradiation of the photoelectric element 18 during the relevant phase. Now if the irradiation of the photoelectric element 18 during both of the pulse phases differs, then both of the capacitors 75 and 76 are differently charged and a voltage appears between both capacitors which constitutes the difference of the irradiation of the photoelectric element in both extreme positions. A relay 77 connected between both of the capacitors 75 and 76 is energized as soon as the charging difference of both capacitors 75 and 76 has exceeded a predetermined threshold value. Consequently, the relay contact 78 is closed and the alarm device 79 which is connected with such contact 78 is energized or activated. As already mentioned, there is simultaneously connected at the pulse transmitter 23, by means of its output line 80, the radiation source 2 and the electromagnet 22 (FIG. 3) or 30 (FIG. 4) for moving the related optical system or element.

The aforedescribed relay devices 55, 65 and 77 furthermore can be randomly constructed, i.e., instead of using electromagnetic relays there can be advantageously employed also other known electronic switching devices or circuits.

While there are shown and described present preferred embodiments of the invention, it is to be distinctly understood that the invention is not limited thereto, but may be otherwise variously embodied and practiced within the scope of the following claims. Accordingly,

What I claim is:

1. A smoke detector comprising:
   a radiation source producing a directed radiation beam;
   a scattered radiation-receiver arrangement having directional characteristics for receiving radiation transmitted by said radiation source;
   an evaluation circuit operatively connected with said scattered radiation-receiver arrangement for delivering a signal when the radiation scattering at smoke particles in the radiation beam exceeds a predetermined value;
   at least any one of said radiation source and said scattered radiation-receiver arrangement have such a directional characteristic and said evaluation circuit being structured such that radiation received from two fields of view of the scattered radiation-receiver arrangement, which fields of view are located differently relative to the radiation beam, can be compared with one another;
   both of the fields of view have a markedly different proportion of scattered radiation, but at least take-up approximately the same spurious radiation from a background constituted by wall means having essentially the same surface properties so as to produce at least approximately the same spurious radiation; and
   both of said fields of view being aligned towards said background.

2. The smoke detector as defined in claim 1, wherein:
   said scattered radiation-receiver arrangement has two radiation receiving elements which receive radiation from said fields of view which constitute two different fields of view;
   one of the fields of view at least partially passing through the radiation beam and receiving the scattered radiation emanating therefrom; and
   the other field of view encompassing a region neighboring the radiation beam.

3. The smoke detector as defined in claim 2, further including:
   a respective lens provided for each of the radiation receiving elements for focusing the related field of view.

4. The smoke detector as defined in claim 2, further including:
   a common collecting lens provided for both of the radiation receiving elements;
   both of said radiation receiving elements being arranged neighboring one another.

5. The smoke detector as defined in claim 1, further including:
   a housing providing a chamber for receiving an external atmosphere containing smoke to be detected;
   said housing having wall portions constituting at least part of said wall means and which are detected by both of said fields of view;
   said wall portions overlapping one another.

6. The smoke detector as defined in claim 1, wherein:
   said radiation source delivers a radiation beam composed of essentially parallel rays of radiation.

7. The smoke detector as defined in claim 6, wherein:
   said radiation source is a laser.

8. The smoke detector as defined in claim 1, wherein:
   said radiation source comprises a radiation-emitting element; and
   a focusing optical system provided for said radiation-emitting element.

9. The smoke detector as defined in claim 1, wherein:
   said fields of view of the scattered radiation-receiver arrangement comprise essentially parallel beams.

10. The smoke detector as defined in claim 1, further including:
    means for focusing one field of view at the radiation beam.

11. The smoke detector as defined in claim 10, wherein:
    said focusing means focus said one field of view at a point common with the radiation beam.

12. The smoke detector as defined in claim 1, further including:
    means for focusing one field of view at the direct neighborhood of the radiation beam.

13. The smoke detector as defined in claim 1, wherein:
    the lengthwise axis of the radiation beam and the lengthwise axis of one of the fields of view receiving scattered radiation from the radiation beam enclose an angle with one another which exceeds 90°.

14. The smoke detector as defined in claim 2, wherein:
    said evaluation circuit comprises a difference circuit connected with both of the radiation receiving elements;
    said difference circuit having an output;
    said difference circuit delivering at its output a signal as a function of the difference of output signals received from the radiation receiving elements.

15. The smoke detector as defined in claim 1, further including:
    light impervious and air pervious housing means enclosing the radiation beam and with said fields of view.

16. The smoke detector as defined in claim 15, wherein:
    said housing is structured to be radiation absorbent at least at any one of the points of impact of the radiation beam and the fields of view.

17. The smoke detector as defined in claim 1, further including:
    alarm circuitry with which there is connected said evaluation circuit;
    said alarm circuitry triggering a signal whenever an output signal of the evaluation circuit exceeds a predetermined threshold value.

18. A smoke detector comprising:
    a radiation source producing a directed radiation beam;
    a scattered radiation-receiver arrangement having directional charactersitics for receiving radiation transmitted by said radiation source;
    an evaluation circuit operatively connected with said scattered radiation-receiver arrangement for delivering a signal when the radiation scattering at smoke particles in the radiation beam exceeds a predetermined value;
    at least any one of said radiation source and said scattered radiation-receiver arrangement have such a directional characteristic and said evaluation circuit being structured such that radiation received from two fields of view of the scattered radiation-receiver arrangement, which fields of view are located differently relative to the radiation beam, can be compared with one another;

both of the fields of view have a markedly different proportion of scattered radiation, but at least take-up approximately the same spurious radiation from at least approximately the same background;

said scattered radiation-receiver arrangement further having two radiation receiving elements which receive radiation from said fields of view which constitute two different fields of view;

one of the fields of view at least partially passing through the radiation beam and receiving the scattered radiation emanating therefrom;

the other field of view encompassing a region neighboring the radiation beam;

a housing having wall means and enclosing a chamber for receiving an external atmosphere containing smoke to be detected;

both of said fields of view of both radiation receiving elements being aligned with the same wall section of said wall means of said housing.

19. The smoke detector as defined in claim 18, wherein:

said same wall section is structured to be radiation-absorbent.

20. A smoke detector comprising:

a radiation source producing a directed radiation beam;

a scattered radiation-receiver arrangement having directional characteristics for receiving radiation transmitted by said radiation source;

an evaluation circuit operatively connected with said scattered radiation-receiver arrangement for delivering a signal when the radiation scattering at smoke particles in the radiation beam exceeds a predetermined value;

at least any one of said radiation source and said scattered radiation-receiver arrangement have such a directional characteristic and said evaluation circuit being structured such that radiation received from two fields of view of the scattered radiation-receiver arrangement, which fields of view are located differently relative to the radiation beam, can be compared with one another;

both of the fields of view have a markedly different proportion of scattered radiation, but at least take-up approximately the same spurious radiation from at least approximately the same background;

said scattered radiation-receiver arrangement further having two radiation receiving elements which receive radiation from said fields of view which constitute two different fields of view;

one of the fields of view at least partially passing through the radiation beam and receiving the scattered radiation emanating therefrom;

the other field of view encompassing a region neighboring the radiation beam;

means defining a wall element having the same properties and with which there are aligned both of said fields of view.

21. A smoke detector comprising:

a radiation source producing a directed radiation beam;

a scattered radiation-receiver arrangement having directional characteristics for receiving radiation transmitted by said radiation source;

an evaluation circuit operatively connected with said scattered radiation-receiver arrangement for delivering a signal when the radiation scattering at smoke particles in the radiation beam exceeds a predetermined value;

at least any one of said radiation source and said scattered radiation-receiver arrangement have such a directional characteristic and said evaluation circuit being structured such that radiation received from two fields of view of the scattered radiation-receiver arrangement, which fields of view are located differently relative to the radiation beam, can be compared with one another;

both of the fields of view have a markedly different proportion of scattered radiation, but at least take-up approximately the same spurious radiation from at least approximately the same background;

means for displacing at least part of the scattered radiation-receiving arrangement into two extreme positions for producing said two fields of view from a common field of view of the scattered radiation-receiving arrangement;

the field of view in the one extreme position detecting part of the radiation beam whereas the field of view in the other extreme position being located externally of the radiation beam.

22. The smoke detector as defined in claim 21, wherein:

said scattered radiation-receiver arrangement comprises a radiation receiving element and a focusing optical element; and said displacing means moving at least one of said elements into said two extreme positions.

23. The smoke detector as defined in claim 21, further including:

a pulse transmitter;

said displacing means including mechanism controlled by said pulse transmitter for the periodic shifting of at least part of the scattered radiation-receiver arrangement for producing said two fields of view from said common field of view.

24. The smoke detector as defined in claim 23, wherein:

said pulse transmitter periodically delivers alternating pulses of positive and negative polarity to said mechanism.

25. The smoke detector as defined in claim 23, wherein:

said pulse transmitter further controls said radiation source.

26. A smoke detector comprising:

a radiation source producing a directed radiation beam;

a scattered radiation-receiver arrangement having directional characteristics for receiving radiation transmitted by said radiation source;

an evaluation circuit operatively connected with said scattered radiation-receiver arrangement for delivering a signal when the radiation scattering at smoke particles in the radiation beam exceeds a predetermined value;

at least any one of said radiation source and said scattered radiation-receiver arrangement have such a directional characteristic and said evaluation circuit being structured such that radiation received from two fields of view of the scattered radiation-receiver arrangement, which fields of view are located differently relative to the radiation beam, can be compared with one another;

both of the fields of view have a markedly different proportion of scattered radiation, but at least take-up approximately the same spurious radiation from at least approximately the same background;

means for shifting the radiation beam into two extreme positions.

27. The smoke detector as defined in claim 26, wherein:

said radiation source comprises a radiation-emitting element and a focusing optical element; and said shifting means including means for moving at least one of both elements into two extreme positions.

28. A smoke detector comprising:

a radiation source producing a directed radiation beam;

a scattered radiation-receiver arrangement having directional characteristics for receiving radiation transmitted by said radiation source;

an evaluation circuit operatively connected with said scattered radiation-receiver arrangement for delivering a signal when the radiation scattering at smoke particles in the radiation beam exceeds a predetermined value;

at least any one of said radiation source and said scattered radiation-receiver arrangement have such a directional characteristic and said evaluation circuit being structured such that radiation received from two fields of view of the scattered radiation-receiver arrangement, which fields of view are located differently relative to the radiation beam, can be compared with one another;

both of the fields of view have a markedly different proportion of scattered radiation, but at least take-up approximately the same spurious radiation from at least approximately the same background;

said scattered radiation-receiver arrangement includes a radiation receiving element;

said evaluation circuit contains means for forming the change of the output signal of the radiation receiving element upon shifting of any one of a common field of view of the scattered radiation-receiver arrangement or the radiation beam from one extreme position into another extreme position.

29. A smoke detector comprising:

a radiation source producing a directed radiation beam;

a scattered radiation-receiver arrangement having directional characteristics for receiving radiation transmitted by said radiation source;

an evaluation circuit operatively connected with said scattered radiation-receiver arrangement for delivering a signal when the radiation scattering at smoke particles in the radiation beam exceeds a predetermined value;

at least any one of said radiation source and said scattered radiation-receiver arrangement have such a directional characteristic and said evaluation circuit being structured such that radiation received from two fields of view of the scattered radiation-receiver arrangement, which fields of view are located differently relative to the radiation beam, can be compared with one another;

both of the fields of view have a markedly different proportion of scattered radiation, but at least take-up approximately the same spurious radiation from at least approximately the same background;

said scattered radiation-receiver arrangement includes a radiation receiving element;

means for selectively shifting a common field of view of the scattered radiation-receiver arrangement or the radiation beam; and said evaluation circuit evaluating an alternating current voltage part of the output voltage of the radiation receiving element.

30. The smoke detector as defined in claim 29, wherein:

said means for selectively shifting periodically shifts the common field of view or the radiation beam.

* * * * *